United States Patent [19]

Voelker et al.

[11] Patent Number: 5,777,210
[45] Date of Patent: Jul. 7, 1998

[54] OIL QUALITY SENSOR MEASURING BEAD VOLUME

[75] Inventors: Paul J. Voelker, Fremont; Joe D. Hedges, Portola Valley, both of Calif.

[73] Assignee: Voelker Sensors, Inc., Palo Alto, Calif.

[21] Appl. No.: 730,109

[22] Filed: Oct. 15, 1996

Related U.S. Application Data

[63] Continuation-in-part of Ser. No. 637,878, Apr. 25, 1996.

[51] Int. Cl.$^6$ .......................... G01N 27/26; G01N 33/30
[52] U.S. Cl. .................. 673/53.05; 204/409; 324/449; 324/663; 324/698; 338/96; 422/82.01; 422/82.02; 200/61.04; 200/61.05
[58] Field of Search .................. 73/53.01, 53.05, 73/61.41, 64.53; 204/400, 409, 410, 421, 422; 422/82.01, 82.02; 324/439, 446–449, 663, 698; 338/38, 44, 96; 200/61.04, 61.05, DIG. 41; 340/627, 631

[56] References Cited

U.S. PATENT DOCUMENTS

| | | |
|---|---|---|
| 2,862,859 | 12/1958 | Grosskopf . |
| 3,182,255 | 5/1965 | Hopkins et al. . |
| 3,410,780 | 11/1968 | Holden . |
| 3,787,650 | 1/1974 | Lewis ...................... 200/61.04 |
| 4,007,629 | 2/1977 | Hochstein . |
| 4,443,754 | 4/1984 | King . |
| 4,606,222 | 8/1986 | Stockmeyer . |
| 4,646,070 | 2/1987 | Yasuhara et al. . |
| 4,733,556 | 3/1988 | Meitzler et al. . |
| 4,764,258 | 8/1988 | Kauffman . |
| 4,791,374 | 12/1988 | Yodice et al. . |
| 4,952,868 | 8/1990 | Scherer, III . |
| 5,071,527 | 12/1991 | Kauffman . |
| 5,089,780 | 2/1992 | Megerle . |
| 5,141,717 | 8/1992 | McRae ........................ 422/82.01 |

FOREIGN PATENT DOCUMENTS 939049  10/1963  United Kingdom ............... 200/61.04

OTHER PUBLICATIONS

Mike Allen, "CAR CLINIC –Dirty Deads Done Dirt Cheap", Popular Mechanics, Aug. 1993, p. 71.

*Primary Examiner*—Hezron E. Williams
*Assistant Examiner*—Daniel S. Larkin
*Attorney, Agent, or Firm*—Skjerven, Morrill, MacPherson, Franklin & Friel LLP; Norman R. Klivans

[57] ABSTRACT

Method and apparatus for determining deterioration of e.g. lubricating oil by measuring the contraction of a polymeric matrix (support) holding charged ionic groups. The support contracts due to oil quality degradation. The expansion/contraction is detected e.g. electrically.

8 Claims, 4 Drawing Sheets

OIL QUALITY SENSOR MEASURING BEAD VOLUME

CROSS REFERENCE TO RELATED APPLICATION

This application is a continuation-in-part of U.S. patent application Ser. No. 08/637,878 filed Apr. 25, 1996.

BACKGROUND OF THE INVENTION

1. Field of the Invention

This invention relates to measurement and testing for liquid analysis, and more particularly to determining electrically the quality of any natural or synthetic oil, oil substitute, oil including additives, or any other non-polar or weakly polar liquid.

2. Description of the Related Art

Commonly invented U.S. Pat. No. 5,435,170, incorporated herein by reference in its entirety, describes a method and apparatus to determine the quality of a fluid, e.g. oil, by its solvating effect on an insoluble (resin) matrix to which charged ion groups have been covalently bound. The solvating effect is measured as a variation in an electrical characteristic (e.g. capacitance or conductivity or impedance) of the matrix. The apparatus in one embodiment includes a housing holding a conductive mesh containing small (milligram) amounts of ion-charged resin beads. A metal probe is fitted in the mesh and makes contact with the resin. The entire apparatus is immersed in the fluid so the fluid enters the housing, and the electrical characteristic is measured from the probe to the mesh through the resin. Fluid quality degradation is measured as a change in electrical conductivity or capacitance through the resin with respect to an increase in the fluid's solvent polarity.

The present inventors have discovered several improvements for their earlier oil quality sensor. These improvements improve the utility and applications of the oil quality sensor which measures typically oil oxidation or additive depletion in real time and can be used to predict the level of degradation of an oil over the normal operating temperature range of a vehicle. It has been found that it would be desirable to improve and extend the utility of that oil quality sensor in terms of the chemistry of the resin beads, sensitivity and dynamic range by the of the sensor, oil contaminant detection, and to adapt the oil quality sensor to become an oil level sensor.

SUMMARY

In accordance with the present invention, the expansion/contraction of the resin beads due to contact with oil of varying quality is exploited mechanically. The beads are enclosed in a flexible enclosure; as they expand (or contract) the resulting change in size of the enclosure is detected e.g. electrically, and used to indicate oil quality. In one embodiment the enclosure is inside a spring loaded housing; as the enclosure contracts, the resulting change in length of the housing is detected electrically by a sliding contact on a resistive member attached to the housing.

Also in accordance with the present invention the method and apparatus disclosed in the above-referenced patent, which use a matrix of polystyrene (resin) beads to conduct a charge when the amount of conductivity and/or capacitance reflects the condition of the oil, first is subject to a chemical process improvement whereby a polar environment is created locally around the charged groups of the resin beads. This polar environment promotes charge separation or dissociation between the cation and anion of the charged groups. This amplifies the signal and improves the sensitivity of the sensor. This is accomplished by pretreating the resin beads with a high boiling point polar protic solvent, such as ethylene glycol.

Also in accordance with the present invention, the dynamic range of the sensor is improved by exploiting the fact that the physical size of the beads changes (becomes smaller) as the fluid changes from a non-polar towards a polar type fluid. The decreasing bead size has been found to decrease the physical contact between the charged groups on the beads which in turn causes a change in the electrical properties (e.g. a decrease in conductivity).

Also in accordance with the invention, the beads are housed in a permeable container so as the beads decrease in size (due to the fluid changing to be more polar) they will filter through the container, so sensor sensitivity is improved. In one embodiment multiple sensor chambers are used with intervening filters each having specific mesh sizes to measure specific levels of fluid polarity.

It has also been found that the beads may be loaded into the sensor at an initial particular size, such that after being immersed in a more non-polar liquid (e.g. oil) the beads expand, forcing better physical contact between them.

In another embodiment, the beads are loaded into the sensor in a highly swollen state and as the fluid (e.g. oil) in which they are immersed becomes more polar their conductivity decreases. Other modifications are also possible utilizing bead swelling and shrinking depending on the condition of the surrounding fluid (e.g. oil). For instance, a spring loaded diaphragm may push on the beads thus maintaining their electrical conductivity. The travel limit of the spring can be set such that it will stop before the beads are at their minimum diameter (corresponding to a specific polar condition). This configuration allows the signal to remain relatively constant over a predetermined range of polarity (clean oil to a specified wear state). Once the bead diameter contracts (corresponding to a further change in polarity) such that the spring tension is no longer requiring physical contact of the beads with each other, the electrical conductivity of the system will degrade rapidly.

In accordance with another aspect of the present invention, it has been found when the oil contains heterogenous contaminants in the form of bubbles or droplets that have a different polarity than does the oil, i.e. when water, anti-freeze, fuel, or even metals become mixed with the oil, the transient behavior of the droplets as they pass through the sensor generates electrical noise in the sensor output signal. The frequency and amplitude of the noise is directly correlated to the amount of contamination, and hence heterogeneous oil contamination by water or other substances is detectable.

Also in accordance with the invention, if the contaminating material happens to be mixed uniformly into the oil to form a homogenous fluid, this is sensed by providing two sensors with beads each having been pretreated with different materials (e.g. polar protic solvents such as ethylene glycol and methanol). Over the course of oil degradation, one set of treatedbeads/sensor causes a decrease in conductivity while the second set of treated-beads/sensor causes an increase in conductivity. Thus when the conductivity measured by the two sensors diverges this clearly indicates contamination.

Also in accordance with the present invention, the beads in two sensors are treated with two different cations or other charged groups, which gives the electrical output signal of each sensor a specific signature as it tracks oil degradation, and the output signals of the two sensors are compared. For instance, iron or lead is thereby easily sensed in the oil indicating excessive engine wear and/or oil degradation.

In accordance with yet another aspect of the present invention, a multi-chamber sensor with the chambers arranged vertically, each containing charged groups in a matrix and its own sensor electrode(s), is used to sense a level of the oil, for instance in the oil pan of an automobile, to determine a low oil condition. The chambers are positioned so that they are at various levels in the oil pan; the absence of oil from any one of the chambers is easily sensed electrically due to the conductivity difference compared to a reference sensor constantly immersed in the oil.

It is to be understood that while the following description is of an oil sensor, the invention is not so limited, and includes method and apparatus for sensing properties of other suitable fluids and also is not limited to automotive or motor applications.

DETAILED DESCRIPTION

Figure 1:
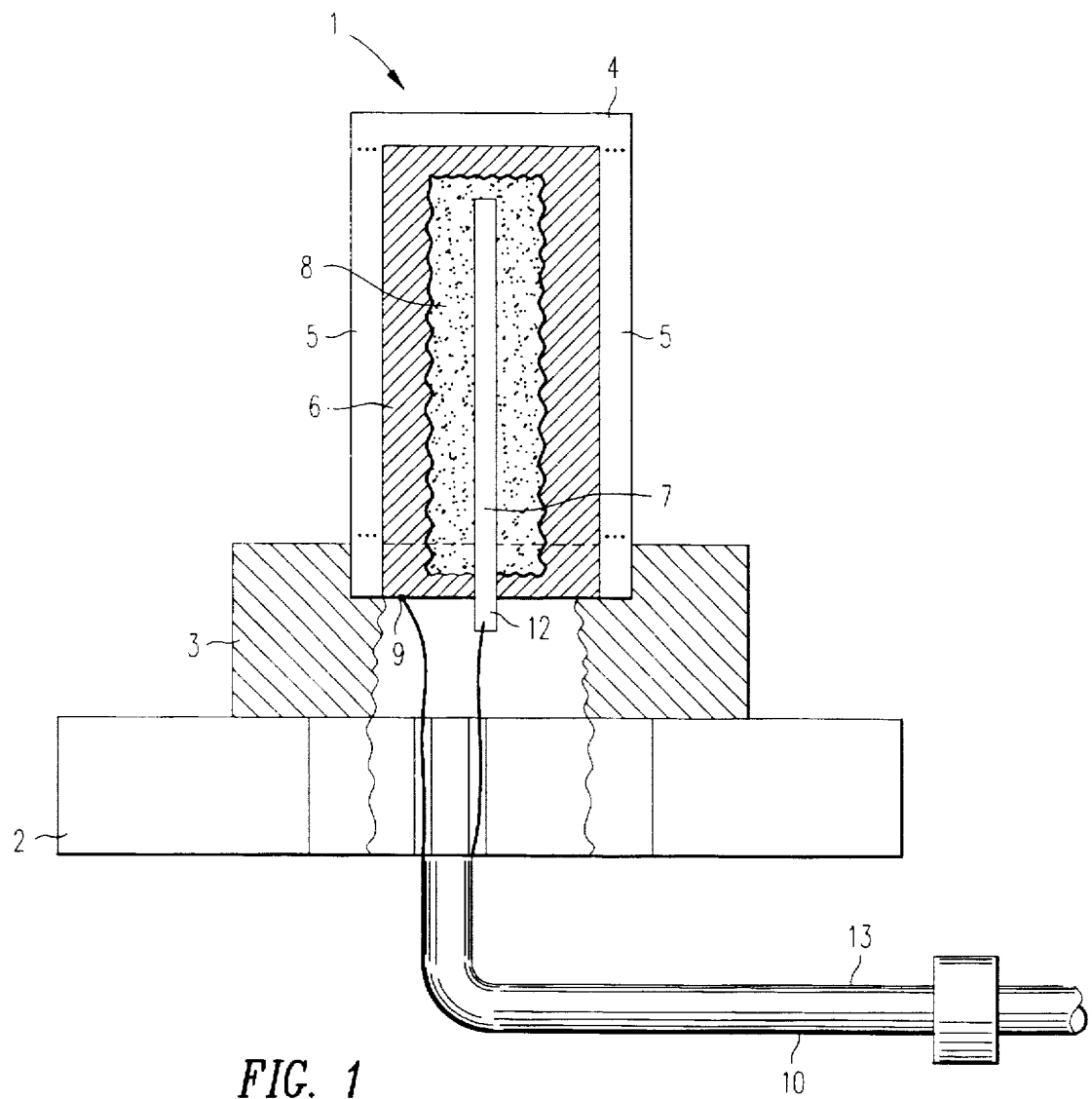
FIG. 1 is a cross-sectional view of an oil quality sensor assembly from the above-referenced patent and also in accordance with this invention.

An oil quality sensor in accordance with the present invention is in many respects similar to that disclosed in the above-referenced U.S. Pat. No. 5,435,170. Hence present FIG. 1 is a cross-sectional view of an oil quality sensor identical to FIG. 1 of that patent in which oil quality sensor 1 is mounted in an otherwise conventional drain plug 2 used in the oil pan of an internal combustion engine i.e. an automobile engine. The drain plug 2 with its standard hex nut arrangement and associated threaded surface 3 are shown as the chief mounting for the oil quality sensor. The e.g. plastic housing 4 provides the outer contaminant for conventional stainless steel wire mesh 6, which in turn holds the polystyrene resin beads 8 impregnated with the charged ion groups, in one embodiment sodium as the cation and sulfite as the anion, with the sulfite covalently bound to the beads. A typical amount of beads is 20 to 500 mg (not limiting). The beads are e.g. cross-linked with 8% cross-linked divinyl benzene and have a titer or exchange capacity of 1.7 meq/ml, each bead being of e.g. 16–400 wet mesh size (1,180 to 38 μm diameter). (The divinyl benzene may be e.g. 0% to 12% cross-linked). Further details of the beads are disclosed in the above-referenced patent application. Also, other types of support and other suitable cation exchange groups may be used.

Opening 5 allows oil to flow through the mesh 6 and the resin beads 8. Although not shown, a similar opening on the opposite side of a housing 4 allows a flow-through arrangement. The metal probe 7 is one electrode of the electrical circuit for measuring the desired electrical characteristic through the resin matrix. Wire 13 is connected at point 12 and routed to the external plug 11 via a conventional oil-tight seal (not shown). Wire 10 is connected to the mesh 6 at point 9 and routed to the external plug 11, also via an oil-tight seal (not shown). It can be seen that the mesh is the second electrode of the electrical circuit for measuring the electrical characteristic through the resin matrix. Plug 11 connects the sensor to the external signal conditioning circuit.

One variant of the sensor of FIG. 1 (not shown) includes a small nonconductive strip of material (e.g. plastic) defining two holes. The strip is covered on each side with a mesh of e.g. stainless steel cloth; each hole holds a quantity of the beads. A cover defining several slots encloses this assembly, which is mounted in an oil pan drain plug. While one hole in the strip allows the engine oil to flow freely through the beads, the other hole is permanently sealed with clean oil trapped inside to act as the internal standard (reference). Thus electrical connections are provided to the beads in each hole.

The slots in the cover in one embodiment are offset (located away from) the bead location to minimize oil flow past the beads, thereby to prevent loss of bead physical contact due to oil circulation.

Figure 2:
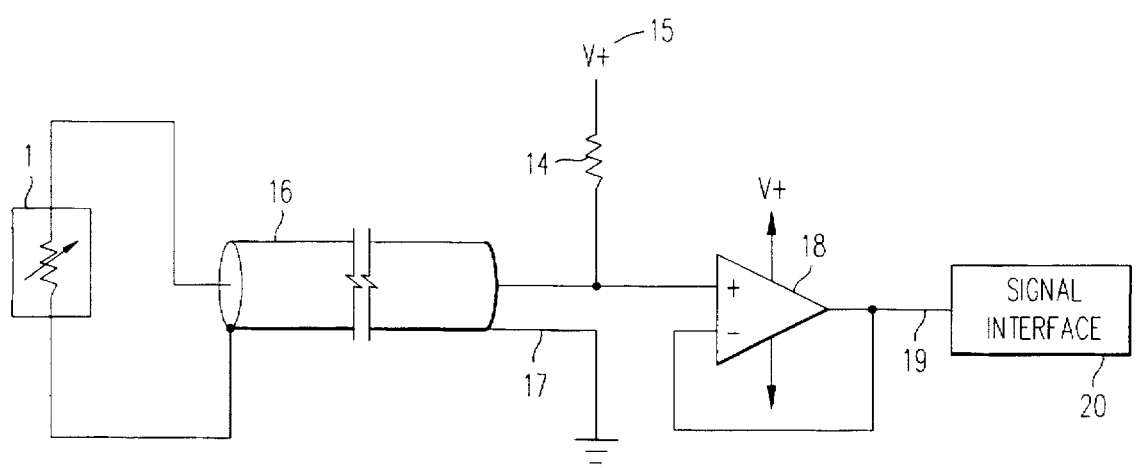
FIG. 2 is a schematic diagram of the oil quality sensor assembly and associated circuitry from the above-referenced patent.

FIG. 2 is a schematic diagram of the oil quality sensor system of the above-referenced patent, herein measuring conductivity as an illustration. Other electrical characteristics could be used alternatively, such as capacitance. The positive voltage V+ at node 15 causes an electric current to flow through a voltage divider consisting of resistor 14 and sensor element 1. Coaxial cable 16 reduces the effect of outside electrical noise on the signal from the remotely located sensor element 1. The resulting voltage developed across the sensor element where the other terminal of coaxial cable 16 is connected to ground at node 17, which is referenced to voltage V+ is applied to the noninverting input of the voltage follower circuit 18.

Voltage follower circuit 18 is a high input impedance amplifier, such as an RCA CA3140 integrated circuit. Such a voltage follower circuit is used because of the very high impedance exhibited by the sensor element under normal operating conditions; any loading of the circuit by an external measuring means would affect the accuracy of the subsequent voltage readings.

The voltage output at node 19 from voltage follower 18 as shown is applied to a conventional signal interface circuit 20. Details of the signal interface are given in the above-referenced patent and may include for instance a simple analog meter, or an analog to digital converter whose output signal is supplied to a microprocessor system for further conditioning and subsequent output to a conventional display.

In a first improvement in accordance with the present invention, a polar environment is created locally surrounding the charged groups of the beads. ("Beads here refers generally to the support, of whatever structure.) This polar environment promotes charge separation or dissociation between the cation and anion of the charged groups. This amplifies the signal and improves the sensitivity or resolving capabilities of the sensor. Creating and maintaining a polar environment around the charged groups in a non-polar environment (e.g. uncontaminated clean oil) is accomplished in accordance with the present invention by pretreating the beads (before being loaded into the sensor, i.e. during manufacture of the sensor) with e.g. a high boiling point polar protic solvent such as ethylene glycol. A protic solvent forms hydrogen bonds with the sulfonyl group of sulfonic acid salt (cation) even at temperatures of up to 1500° C., thereby creating the desired local polar environment. This has been found to increase resolution by creating an amplified sensor output signal.

The actual process of preparing the beads involves washing the beads with 1N sodium hydroxide for about 15 to 30 minutes at room temperature. The excess sodium hydroxide is washed off in methanol. The beads are then soaked in methanol to remove any excess water, then air dried to remove any remaining methanol. The beads are then soaked in the ethylene glycol for e.g. 24 hours, and heated to 120° C. for about 2 hours to ensure penetration of the ethylene glycol. The beads so treated are fully swollen.

Last, the beads are placed in clean oil (or another non-polar fluid) and heated to 120° C. to remove any excess ethylene glycol and shrink the beads down to their "clean oil" state. The beads are then loaded into the sensor under slight pressure so they are in close contact with one another. Alternatively, the beads are soaked in the ethylene glycol after being loaded into the sensor.

Beads so treated have been found advantageously to improve the signal strength from the sensor one to two orders of magnitude. What is occurring in terms of electrochemistry is that the hydrogen of the ethylene glycol bonds to the oxygen of the bead resin, creating the desired localized polar environment. The relatively high boiling point is desirable because lower boiling point substances might boil off when the oil becomes hot in the engine environment.

In accordance with another aspect of the present invention, the present inventors have used the extent of bead swelling and shrinkage to determine solvent/liquid polarity. (Cross-linking of the beads increases rigidity of the resin matrix and increases the number of divinyl benzene groups.) In this approach the beads shrink in size with increasing oil polarity (i.e. degrading of the oil) and the beads then physically pass through a mesh (filter) and collect in a lower chamber. The collecting chamber produces an electrical signal from its electrodes as affected by the quantity of beads present, which serves to confirm the measured oxidation of the oil. Hence it has been found that as the fluid changes from a non-polar towards a polar one, the diameter of the beads exposed to the oil becomes smaller (the beads shrink). Decreasing the size of the beads has been found to affect the contact between the charged groups which in turn changes the electrical properties of the beads (e.g. decreases conductivity). By selecting for instance a permeable container containing a fine meshed filter which corresponds to the size of the beads, one may insure that when the beads are in a non-polar environment (clean oil) they will not pass through the filter.

Figure 3C:
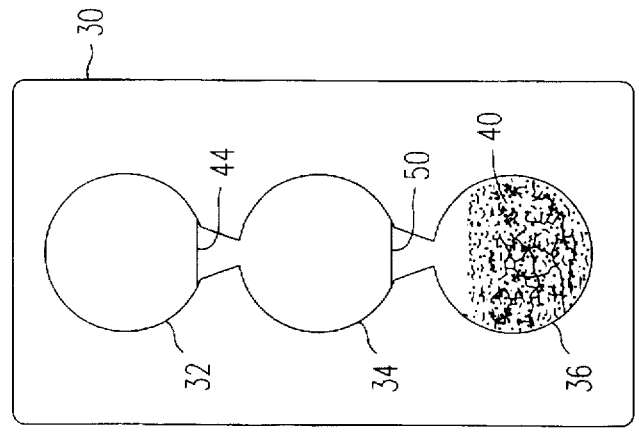
FIG. 3C shows the chamber of FIG. 3A with the beads in the lowest chamber.
Figure 3B:
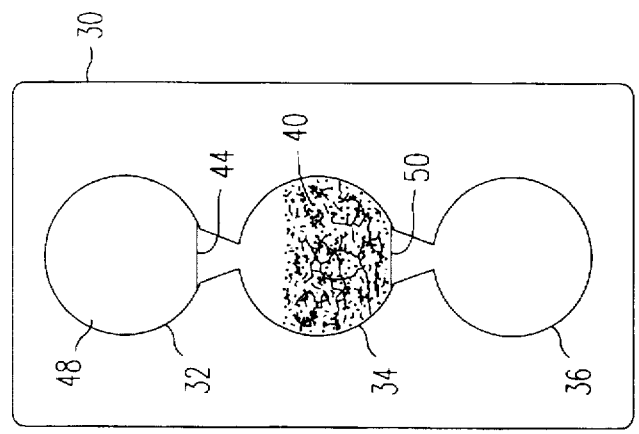
FIG. 3B shows the chamber of FIG. 3A with the beads in the central chamber.
Figure 3A:
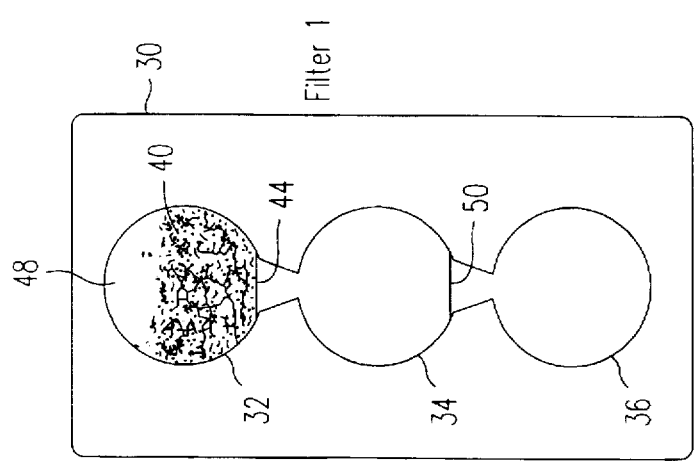
FIG. 3A shows a three-chamber oil sensor in accordance with the present invention.

An example of such a sensor is shown diagrammatically in FIG. 3A where a three-chamber housing 30 for the oil quality sensor has chambers 32, 34 and 36. Initially the beads 40 (with the charged groups) are located in chamber 32 and are held therein by a suitable filter or mesh 44. As the oil 48 (which circulates through all three chambers 32, 34, 36) degrades, i.e. becomes more polar, the bead diameter decreases and due to gravity the beads 40 pass through the filter 44 into the second chamber 34, as shown in FIG. 3B, thereby causing a decrease in conductivity in the first chamber 32 as the beads 40 are eliminated therefrom. There is a corresponding increase in conductivity in the second chamber 34 as the beads 40 enter that chamber 34. It is to be understood that each chamber 32, 34, 36 is equipped with two electrodes (not shown), for instance a probe and a second electrode which might be the filter mesh. The corresponding signal processing circuitry is not shown but its nature will be readily understood by one skilled in the art in light of the above-referenced patent.

As the beads 40 pass, under the influence of gravity and the oil circulation, from the first chamber 32 down to the lower second chamber 34, there is a substantial decrease in the strength of the conductivity signal across the electrodes of the first chamber 32 versus those of the second chamber 34. This greatly increases the sensing dynamics of the system and makes signal sensing relatively easy. This method also allows detection of oil reaggregation, (the onset of oil sludge). This is because the present inventors have found that as the oil reaggregates, the oil's solvent properties change from a polar state back to a non-polar state which is indicated by an increase in conductivity in any one chamber.

Multiple chambers can be used with a third chamber 36 separated from the second chamber by another filter 50 having yet a finer mesh capacity to measure further shrinkage in the beads 40. As the oil further degrades, the beads 40 pass from the second chamber 34 into the third chamber 36 as shown in FIG. 3C, and the signal strength across the electrodes in the third chamber 36 is measured to indicate this state of the oil. In effect, this multi-chamber oil sensor is an "electromechanical state machine" where the various oil states are determined, not only by the current polar condition of the oil, but also by the previous polar condition of the oil. The state of the oil hence can be measured by monitoring the electrical characteristics of each chamber via its associated electrodes, either directly or through an intervening processor such as a microprocessor programmed to interpret the relative signal strength from the electrodes associated with each chamber and drive a display (e.g. an LED or LCD) indicating visually the corresponding oil condition.

With the multiple chamber approach, the initial size of the beads is controlled to be within a small range to correspond to the initial mesh size. Also for use in a diesel engine (where often soot is present in the lubricating oil) one uses a larger bead size and a larger mesh. This prevents the soot from clogging the mesh.

Also in accordance with the invention, the beads are loaded into the sensor (in this case a single chamber sensor) initially in a non-swollen state such that after being immersed in a more non-polar liquid (cleaner oil, or an oil that contains a higher quantity of non-polar additives), the beads expand, forcing physical contact amongst themselves. The resulting electrical signal from the sensor electrodes remains at the same level of conductivity until the bead's initial loading polar state was achieved again, to indicate a certain degree of oil degradation. Only then would the conductivity be allowed to decrease by separation of the beads due to less physical contact in a more polar condition of the oil. This provides a definite indication of a particular degree of oil degradation.

Conversely, in another version the beads are initially loaded into the sensor in a highly swollen state. After the oil degrades and hence becomes more polar, the sensor conductivity shows a more immediate decrease, hence providing a sharply defined indication of oil degradation and an easily interpreted output signal.

In a third approach utilizing bead swelling and shrinking, the beads are loaded into the sensor to a specified loading quantity (not completely filling the chamber) in the least swollen state. This least swollen state is obtained by initially immersing the beads in a highly polar solution before loading them into the sensor. When the sensor in use is exposed to oil that is less polar, the beads expand, increasing sensor conductivity. Since the additives used in commercial oil change the oil's polarity, the sensor can be loaded initially with beads swollen to a size such that in oil without additives, the sensor is at a known fill level of beads. The sensor can then be placed in the oil with additives in the engine. The change in conductivity due to the beads swelling and shrinking then tracks additive addition and depletion, e.g. in a laboratory environment.

In yet another aspect in accordance with the present invention, the present inventors have found when the oil contains localized contaminants which form droplets having a different polarity than does the oil (contaminants such as water, anti-freeze, fuel, or even metals) the transient behavior of the heterogeneous contaminant droplets as they pass through the sensor causes easily observable electrical noise in the output signal from the sensor electrodes. This would typically occur with a major coolant leak into the engine. The frequency and amplitude of the noise is directly correlated to the quantity of contamination. Quantities of such heterogenous contaminants as little as 2% can be easily detected using this approach. In this case the oil sensor is as shown in FIGS. 1 and 2 with additional output signal processing. This signal processing circuitry looks for noise of a particular amplitude or frequency in the output signal to detect contamination. One signal processing approach is to observe a standard deviation of the signal amplitude or of the signal frequency; this is easily performed by circuitry or in software using a microprocessor connected to the sensor output circuitry, to provide a warning of oil contamination upon detection of a particular frequency or level of electrical noise.

Some contaminating materials may be emulsified into the oil and hence not detectable by this approach. This could occur under some conditions due to water condensation, anti-freeze or fuel contamination. In this case, another approach involves chemically treating the resin beads in two sensors with different charged groups, such that with one charged group conductivity is increased by the contamination while the second charged group in the second sensor beads causes the conductivity to decrease. Both sensors are placed in the oil and their output signals compared. Therefore when the conductivity of the two sensors diverges, contamination is indicated, where the amount of the divergence correlates to the amount of contamination.

Figure 4:
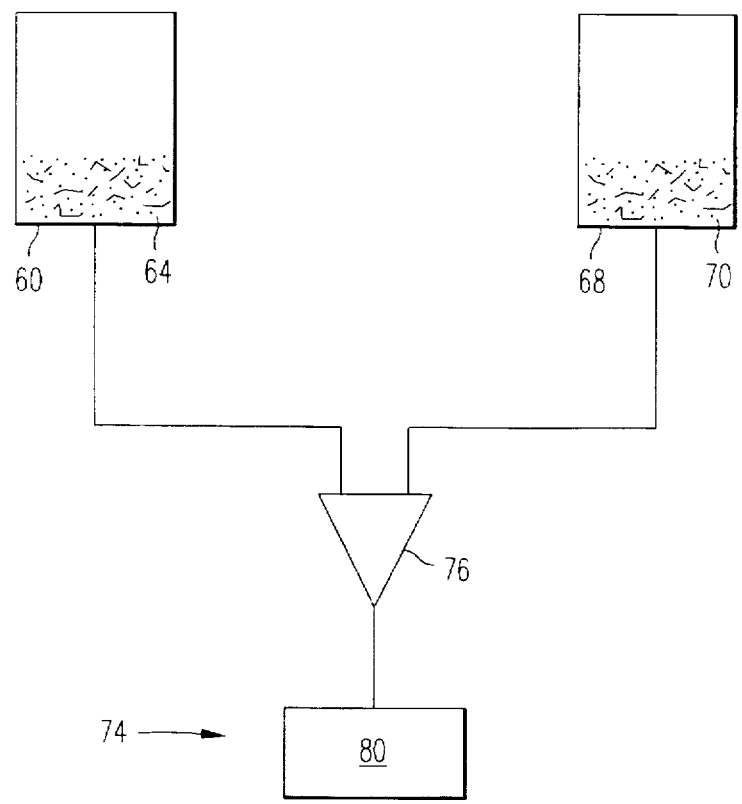
FIG. 4 shows an oil quality sensor device having two sensors with different properties.

This sensor arrangement is shown in FIG. 4 with two sensors 60, 68. The beads 64 in sensor 60 are treated with e.g. sodium as the cation. The beads 70 in sensor 68 are treated with e.g. iron as the cation. Both sensors 60, 68 are exposed to the oil, and the output signals from their electrodes (not shown) are both routed to signal processing circuitry 74, for comparison by comparator 76, the output of which is provided to output circuitry 80 for display to indicate oil contamination. It is to be understood that FIG. 4 is explanatory and not limiting of the two sensor approach.

In accordance with another aspect of the present invention, before being placed into the sensor (during manufacture) the beads are initially treated with a particular charged group, e.g. sodium, which gives the electrical signal a specific signature as it tracks oil degradation. When the sensor is in use, the sodium is displaced by other metal ions from the oil that change the signature of the output signal. Of particular interest would be the electrical signature of iron or lead present in the oil, indicating engine wear due to iron or lead entering the oil from the engine components. Using two differently treated sensors both immersed in the engine oil, such as one treated with sodium and the other treated with iron, the output signals (electrical signatures) of the two sensors are compared for instance by a microprocessor. A sensor of this type would appear to be similar to that of FIG. 4. Initially the signatures of the two sensors would be different. When iron contamination of the oil occurs, the sodium ion in the resin beads in the first sensor is displaced by the iron ion and the signatures from the two sensors would then be the same, indicating oil degradation. The engine iron, copper, lead, zinc, etc. present in the oil is oxidized from a metal state to an ionic state by a compatible charged group and encounters the sodium on the resin beads and displaces it. A zero output from the comparator (see FIG. 4) indicates contamination for instance by copper, zinc, lead, or iron, and excessive engine wear.

One could even determine where the particular wear is occurring in terms of engine components, depending on e.g. the known lead concentration in each various engine component.

Figure 5:
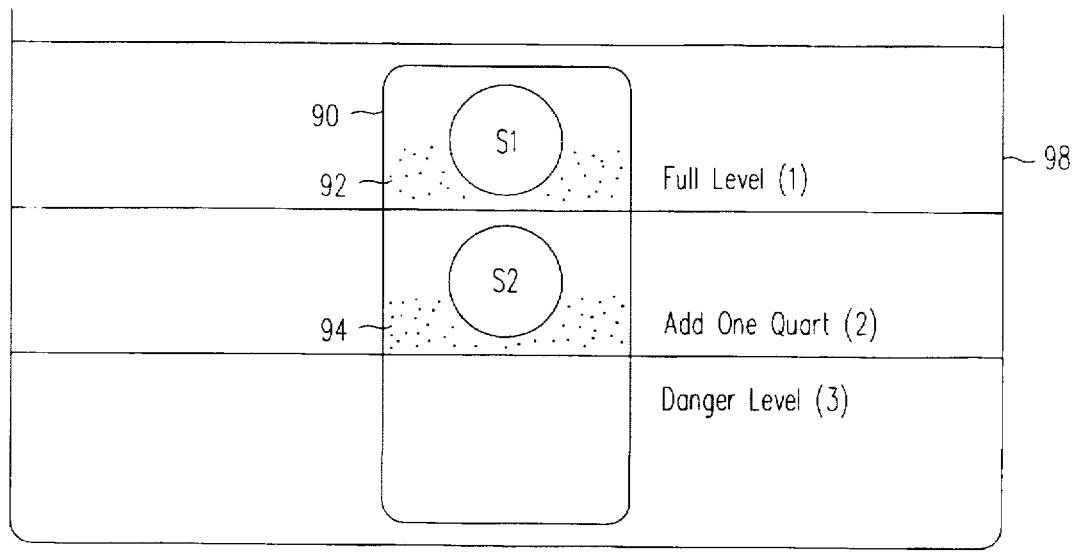
FIG. 5 shows an oil level sensor with multiple chambers in accordance with the present invention.

Also in accordance with the present invention a multi-chamber sensor determines oil level, typically to determine a low oil condition. In this case the entire sensor assembly 90 as shown in FIG. 5 is located in the engine oil pan 98 and arranged vertically. The indicated oil levels are e.g. the oil pan 98 is full, one quart low, or the danger level at which the engine is subject to damage. In this case each sensor chamber S1, S2, S3 is physically isolated from the other and each has its own beads 92, 94 and own sensor electrodes (not shown). Sensor S3 is always immersed in oil and serves as a reference. Hence each chamber by itself is similar to the structure of FIG. 1. It has been found that the signal from a particular sensor is much different when it is immersed in oil compared to when it is in air (when there is no oil at that level). Thus by positioning the chambers S1, S2 at various levels in the oil pan, the oil level can be determined. The sensor electrodes of chambers S1, S2, S3 can be connected electrically in series or in parallel and electrical characteristics of the chambers S1, S2, S3 are measured either collectively or individually.

Thus, in one example a direct current resistance measurement is taken. The typical resistance of clean oil is about 2M ohms at engine operating temperatures. The typical resistance of the beads 92, 94 in air is about 10M ohms. If the electrodes of the two sensors S1, S2 are connected electrically in series the total resistance R is simply that of two resistors in series: $R=R_1+R_2$ For a full oil pan hence the resistance R is: R=2M ohms+2M ohms=4M ohms.

For an oil level that is one quart low, the resistance R is: R=2M ohms+10M ohms=12M ohms.

For the oil level that is dangerously low, the total resistance R is:

R=10M ohms+10M ohms=20M ohms.

In this case, one has three distinct different resistances depending on the oil level to be compared to the resistance of the reference sensor S3. The various chambers need not be connected mechanically (need not share the same housing) although, typically for simplicity they would share a single housing as illustrated in FIG. 4. Also, the sensors alternatively are connected electrically in parallel.

As described above, the resin beads are composed of two functional groups; 1) a hydrophobic component (i.e., the polystyrene/divinyl benzene hydrocarbon backbone) and 2)

a hydrophilic component (i.e., the ionic sodium/sulfonyl bond). The two groups differ in terms of their solvent properties. The hydrophobic component is attracted to or solvated by a nonpolar environment while the hydrophilic component is solvated by a polar environment. Solvation typically results in a sample freely dissolving into solution. In the case of the resin beads, the insoluble nature of the resin matrix prevents the groups attached to the beads from dissolving. Instead, the attached groups expand into the favorable environment (as if dissolving) and take on the behavior of swelling.

Either the hydrophobic or hydrophilic component can contribute to bead swelling. In the case of oil degradation, a clean or nonpolar oil causes bead swelling by solvating the hydrophobic components of the resin. As the oil degrades, the solvent properties change from a nonpolar nature to a polar one, which translates to a loss in salvation and results in bead shrinkage.

Pretreating the beads with ethylene glycol as described above solvates the hydrophilic group. Solvating the hydrophilic portion of the resin has been found to enhance the hydrophobic swelling properties of the beads. Solvating both groups results in effectively extending the swelling ranges of the beads. Ethylene glycol represents a significant improvement in the operation of the sensor by improving both the electrical characteristics and the mechanical (swelling) aspects of the resin used in detecting a change in the solvent properties of an oil.

In accordance with another aspect of this invention, the volume change of the beads is measured, as opposed to the diameter change. A temperature independent method of measuring volume change is used that does not involve the electrical conductivity of the beads. Since the change in volume is approximately four times the change in diameter (i.e., proportional to the cube of the radius), a change in volume is easier to measure. Using this technique, the measurable range is increased and the temperature dependence removed.

The change in volume is measured in one of a variety of ways in which the effect of temperature is negligible. One way is to pack a flexible chamber which is permeable with the resin beads so that the chamber is exposed to oil and use a strain gage to measure the decrease in pressure. As the oil is oxidized, the beads shrink, causing a decrease in pressure; the pressure decrease directly relates to increasing oil oxidation.

Figure 6:
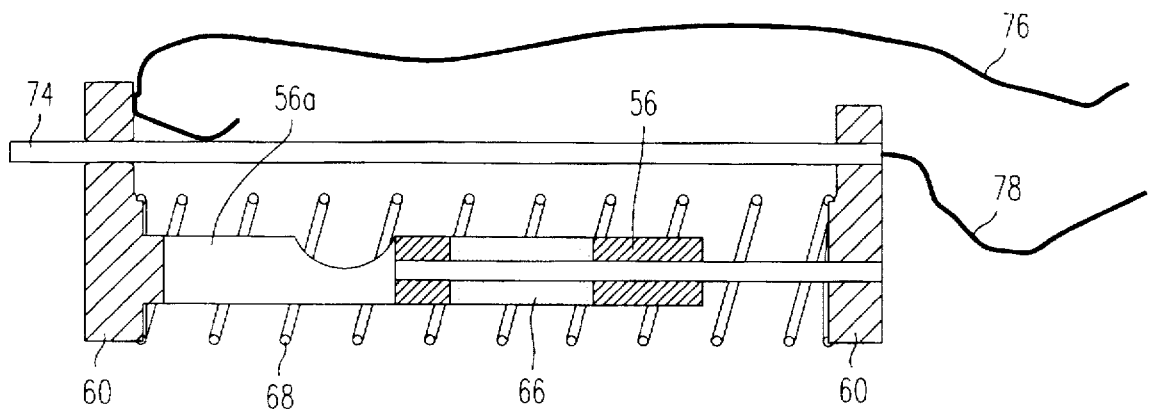
FIGS. 6 and 7 show respectively front and back views of an oil quality sensor that measures bead volume change in accordance with the present invention.
Figure 7:
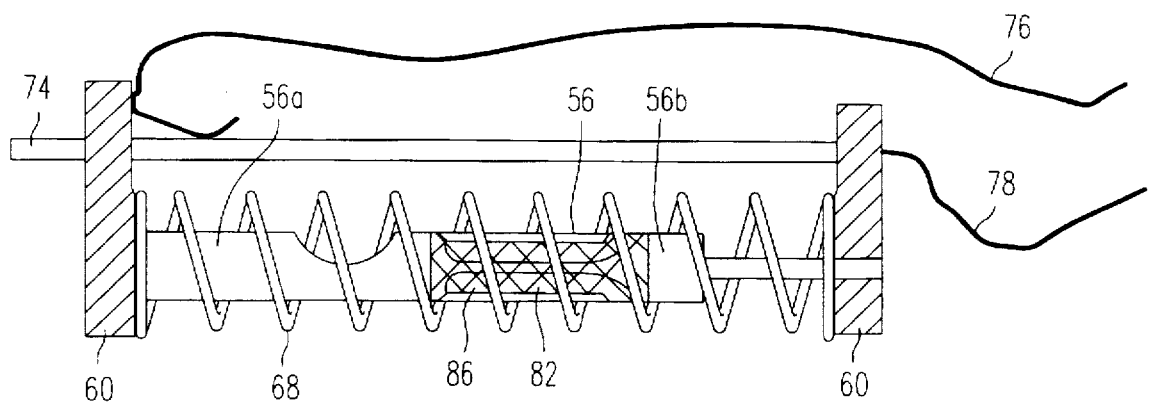

A second method uses a sensor having a linear potentiometer attached to a spring tensioned plunger that is constantly compressing the beads. The beads are contained in a permeable chamber that is exposed to the oxidizing oil. As the plunger moves in response to the volume decrease, the change in resistance of the potentiometer is measured. As shown in front and back views in respectively FIGS. 6 and 7, the potentiometer resistive element 74 is a 1/16" diameter polysulfone rod 56 that has been coated with a carbon (electrically conductive) paint. The housing 60 is of a non-conductive plastic and the permeable chamber 63 is a stainless steel mesh 82. Electrical measurement from one end of the rod 56 to a sliding contact 62 on the housing 60 of the sensor shows the change in resistance as related to the change in volume of the beads 66.

Compression spring 68 pushes apart the two ends of the housing 60. For mechanical purposes, rod 56 includes non-conductive member 56a, 56b at each end. The resin beads are loaded into rod 56 at hole 70. Resistive element 74 lies between electrical leads 76, 78. Hence the bead expansion/contraction is used in a purely mechanical sense to change the length of the resistive element that is in the circuit between leads 76, 78; the amount of resistance thereby indicates the fluid status. The fluid (e.g., oil) enters rod 56 through mesh 82 defining flow slots 86 so as to contact the resin beads.

In another embodiment, rather than electrically measuring the bead contraction, the change in length of rod 56 is measured e.g. optically, using a linear scale and optical encoder.

In another version (not shown but otherwise similar to that of FIGS. 6 and 7), a potentiometer is not necessary. Instead the plunger 74 is made of a conductive material and the housing of a non-conductive material. At a specific point on the housing, a conductive pickup is mounted such that when the beads have decreased in diameter to a specific volume (relating to a specific oxidation state of the oil), the plunger then contacts the conductive pickup, causing a signal to be transmitted indicating that the oil has degraded. As explained herein, many factors contribute to electrical characteristics of the signals output by the oil quality sensor. The bead physical dimensions, the bead size, cross linking of the beads, the initial loading concentration, and the pretreatment of the beads all contribute to the signal output. In accordance with the invention, these parameters are used in various ways in one or more oil quality sensor chambers to optimize the sensitivity of the sensor to various oil conditions for particular applications. Each sensor can be adapted as described above such to allow level sensing in addition to e.g. metal detection and additive depletion. Thus, one may use various combinations of detection features for multiple detectors in a single sensor device.

This disclosure is illustrative and not limiting; further modifications will be apparent to one skilled in the art in light of this disclosure, and are intended to fall within the scope of the appended claims.

We claim:

1. A method of measuring an electrical characteristic of a fluid, comprising the steps of:

providing a quantity of resin beads holding charged groups, the beads each being in a known state;

exposing the beads to a fluid;

allowing a size of the beads to change upon exposure to the fluid, a change in the size of the beads moving a spring loaded member; and measuring a position of the member.

2. The method of claim 1, wherein the size of the beads increases.

3. The method of claim 1, wherein the size of the beads decreases.

4. The method of claim 1, wherein the fluid is a non-polar or weakly polar fluid, and the electrical characteristic indicates an increasing polar nature of the fluid.

5. The method of claim 1, wherein the step of providing includes providing the beads in a known swollen state.

6. The method of claim 1, wherein the step of providing includes providing the beads in a non-swollen state.

7. A fluid sensor comprising:

an enclosure having at least one opening for admitting a fluid into its interior;

a quantity of resin beads inside the enclosure, the enclosure having a spring loaded member in contact with the beads, whereby exposure to the fluid changes a size of the beads, moving the member; and a mechanism coupled to the member and which measures a position of the member.

8. The sensor of claim 7, wherein the mechanism includes an electrically resistive element contacted by a sliding contact coupled to the spring loaded member.

* * * * *

UNITED STATES PATENT AND TRADEMARK OFFICE
CERTIFICATE OF CORRECTION

PATENT NO.    : 5,777,210
ISSUE DATE    : July 7, 1998
INVENTOR(S)   : Paul J. Voelker et al.

It is certified that error appears in the above-identified patent and that said Letters Patent is hereby corrected as shown below:

At column 5, line 6, delete "1500° C.," and substitute --150° C.,--.

At column 9, line 17, delete "salvation" and substitute --solvation--.

Signed and Sealed this

Seventh Day of March, 2000

Attest:

Q. TODD DICKINSON

*Attesting Officer*    *Commissioner of Patents and Trademarks*